United States Patent [19]

Mantegazza et al.

[11] Patent Number: 5,498,793
[45] Date of Patent: Mar. 12, 1996

[54] CATALYTIC PROCESS FOR THE PRODUCTION OF OXIMES

[75] Inventors: Maria A. Mantegazza, Monza; Guido Petrini, Galliate, both of Italy

[73] Assignee: Enichem S.p.A., Milan, Italy

[21] Appl. No.: 463,554

[22] Filed: Jun. 5, 1995

[30] Foreign Application Priority Data

Jun. 9, 1994 [IT] Italy .................................. MI94A1208

[51] Int. Cl.$^6$ ................................................. C07C 249/04
[52] U.S. Cl. ............................................ 564/265; 564/267
[58] Field of Search ..................................... 564/265, 267, 564/259

[56] References Cited

U.S. PATENT DOCUMENTS 4,794,198  12/1988  Roffia et al. ............................ 564/267

OTHER PUBLICATIONS

U.S. patent application Ser. No. 08/39,839—Two-Step Process for Liquid-Phase Production of Oximes, in the names of Maria Angela Mantagazza and Guido Petrini.

*Primary Examiner*—Peter O'Sullivan
*Attorney, Agent, or Firm*—Stevens, Davis, Miller & Mosher

[57] ABSTRACT

Process for the production of oximes which comprises ammoximation of a carbonylic compound selected from acetophenone and cyclododecanone with $H_2O_2$ and $NH_3$ in the presence of a catalyst based on silicon, titanium and oxygen and a cocatalyst consisting of amorphous silica.

10 Claims, No Drawings

CATALYTIC PROCESS FOR THE PRODUCTION OF OXIMES

The present invention relates to a catalytic process for the production of oximes.

More specifically, the present invention relates to a catalytic process for the production of oximes by the reaction in a liquid phase of a carbonylic compound, selected from acetophenone and cyclododecanone, with $NH_3$ and $H_2O_2$.

European patents 208.311, 267.362,299.430 or more specifically, U.S. Pat. No. 4,794,198, describe the preparation of oximes from the corresponding carbonylic compounds, for example cyclohexanone, by reaction with ammonia and hydrogen peroxide in the presence of a catalyst based on silicon, titanium and oxygen. Whereas the preparation of the oxime deriving from cyclohexanone h&s given satisfactory results, in particular when relating to hydrogen peroxide, in the case of other ketones, such as acetophenone or cyclododecanone, the yields and conversions are decisively less favourable.

The Applicant has now found that it is possible to increase the yields and conversions in the synthesis of oximes starting from acetophenone and cyclododecanone if a cocatalyst consisting of amorphous silica is used in addition to the conventional catalyst.

The present invention therefore relates to a process for the production of oximes which comprises ammoximation of a carbonylic compound selected from acetophenone and cyclododecanone with $H_2O_2$ and $NH_3$ in the presence of a catalyst based on silicon, titanium and oxygen and a cocatalyst consisting of amorphous silica.

The reaction is carried out at a temperature of between 50° and 150° C., preferably between 70° and 120° C., under values of autogenous pressure or higher, for example up to 5 bars.

The reaction times are between 1 and 10 hours, preferably between 2 and 5 hours.

According to a preferred embodiment of the process of the present invention, the ammoximation reaction is carried out in the presence of suitable solvents. These solvents, which can be either soluble or insoluble in water, are stable, under reaction conditions, to the action of hydrogen peroxide and are good solvents with respect to the oximes produced. The ratio between solvent and carbonylic compound is generally between 2.5 and 10 by weight.

Examples of suitable solvents for the process of the present invention are tertiary alcohols such as t-butylic or t-amylic alcohols, or $C_1$–$C_6$ aliphatic or cyclo-aliphatic alcohols such as methanol, ethanol, n-butanol and cyclohexanol. Other solvents can be selected from $C_5$–$C_8$ aliphatic or aromatic hydrocarbons such as hexane, benzene, toluene, xylenes, chlorobenzene, their mixtures, etc.

The ammoximation reaction can be indifferently either semi-continuous (with the continuous feeding of the hydrogen peroxide only) or in continuous (with the continuous feeding of all the reagents). It is also preferable to operate with a molar ratio $H_2O_2$/carbonylic compound of between 0.1 and 2 or, more specifically, between 0.4 and 1.2.

The ammonia can be fed to the reaction either in a gas phase or in an aqueous solution. In both cases the concentration of ammonia in the liquid reaction medium is between 0.5 and 15%, preferably between 2 and 10% by weight.

The catalytic system used in the process of the present invention consists of the primary catalyst based on silicon, titanium and oxygen and a cocatalyst consisting of amorphous silica.

As catalyst, titanium-silicalite, whose preparation is described for example, in U.S. Pat. No. 4,410,501 or the mixed oxides $SiO_2$-$TiO_2$ described in European patent 347.926, can be used.

Amorphous silica having a surface area of between 100 and 700 $m^2/g$, can be used as cocatalyst.

To guarantee an effective dispersion of the catalyst in the liquid medium, it is preferable to operate with concentrations of between 1 and 15%, preferably between 1 and 6% by weight, whereas the weight ratio catalyst/cocatalyst can vary from between 0.5 and 10, preferably from between 1 and 5.

The catalyst is dispersed in the reaction medium in the form of crystals, as obtained from the synthesis, or in microspheres having particle dimensions of between 5 and 100 micrometers. The cocatalyst is used in the form of powder or microspheres having the same particle size distribution as the catalyst.

The following examples which are illustrative but not restricting, provide a better understanding of the present invention and enable its embodiment.

EXAMPLE 1

1.5 g of a catalyst consisting of titanium-silicalite in a microspheroidal form with diameters of between 5 and 100 micrometers, prepared according to example 1 of U.S. Pat. No. 4,701,428, 3 g of GRACE 360 silica, 13 $cm^3$ of aqueous ammonia (at 30% by weight), 37 $cm^3$ of t-butanol and 12.02 g of acetophenone were charged, under an inert atmosphere, into a jacketed glass reactor, equipped with a magnetic stirrer.

The suspension was brought to 80° C. and 5.92 g of diluted $H_2O_2$ (at about 30% by weight) were fed, under stirring, in 2.5 hours. At the end of the reaction the suspension was filtered and there was a 33% conversion of the ketone with a selectivity to oxime of more than 99%. The yield of hydrogen peroxide was 64.5%.

EXAMPLE 2

(Comparative)

Example 1 was repeated without adding silica. At the end of the reaction the conversion of the acetophenone was 26.2% with a selectivity to oxime of more than 99%. The yield of hydrogen peroxide was 53%.

EXAMPLE 3

1.5 g of the same catalyst, 1.5 g of GRACE 360 silica, 13 $cm^3$ of aqueous ammonia (at 30% by weight), 37 $cm^3$ of t-butanol and 11.91 g of acetophenone were charged into the reactor of example 1.

The suspension was brought to 80° C., and 11.15 g of diluted $H_2O_2$ (at about 30% by weight) were fed, under stirring, in 2.5 hours. At the end of the reaction the suspension was filtered and there was a 37.7% conversion of the acetophenone with a selectivity to oxime of more than 99%. The yield of hydrogen peroxide was 39.3%.

The same test repeated without adding silica gave a conversion of the acetophenone of 32.7% and a yield of hydrogen peroxide of 33.4%.

EXAMPLE 4

1.5 g of the same catalyst, 1.5 g of GRACE 360 silica, 13 $cm^3$ of aqueous ammonia (at 30% by weight), 37 $cm^3$ of t-butanol and 12 g of acetophenone were charged into the reactor of example 1.

The suspension was brought to 80° C., and 11.12 g of diluted $H_2O_2$ (at about 30% by weight) were fed, under stirring, in 5 hours. At the end of the reaction the suspension was filtered and there was a 55.4% conversion of the acetophenone with a selectivity to oxime of more than 99%. The yield of hydrogen peroxide was 57.6%.

The same test repeated without adding silica gave a conversion of the acetophenone of 50.7% and a yield of hydrogen peroxide of 53.1%.

EXAMPLE 5

1.5 g of the same catalyst, 1.5 g of GRACE 360 silica, 10 $cm^3$ of aqueous ammonia (at 30% by weight), 50 $cm^3$ of t-butanol and 6 g of cyclododecanone were charged into the reactor of example 1.

At 80° C., 4.14 g of diluted $H_2O_2$ (at about 32.5%) were fed, in 8 hours. There was an 85.5% conversion of the cyclododecanone with a selectivity to oxime of more than 99%. The yield of hydrogen peroxide was 71.4%.

The same test repeated without adding silica gave a conversion of the cyclododecanone of 76.6% and a yield of hydrogen peroxide of 65.8%.

EXAMPLE 6

Example 5 was repeated adding 1.5 g of AKZO F7 silica to the catalyst.

The conversion of the cyclododecanone was 85.2% with a selectivity to oxime of more than 99%. The yield of hydrogen peroxide was 72.3%.

We claim:

1. Process for the production of oximes which comprises ammoximation of a carbonylic compound selected from acetophenone and cyclododecanone with $H_2O_2$ and $NH_3$ in the presence of a catalyst based on silicon, titanium and oxygen and a cocatalyst consisting of amorphous silica.

2. Process according to claim 1, wherein the reaction is carried out at a temperature of between 50° and 150° C. under values of autogenous pressure or higher.

3. Process according to claim 1, wherein the ammoximation reaction is carried out in the presence of solvents selected from tertiary alcohols, or $C_1$–$C_6$ aliphatic or cycloaliphatic alcohols and $C_5$–$C_8$ aliphatic or aromatic hydrocarbons.

4. Process according to claim 1, wherein the ration between solvent and carbonylic compound is between 2.5 and 10 by weight.

5. Process according to claim 1, wherein the molar ratio $H_2O_2$/carbonylic compound is between 0.1 and 2.

6. Process according to claim 1, wherein the concentration of ammonia in the liquid reaction medium is between 0.5 and 15%.

7. Process according to claim 1, wherein the catalyst consists of titanium-silicalite or mixed oxides $SiO_2$-$TiO_2$.

8. Process according to claim 1, wherein the cocatalyst is amorphous silica having a surface area of between 100 and 700 $m^2$/g.

9. Process according to claim 1, wherein the weight ratio catatyst/cocatalyst varies from 0.5 to 10.

10. Process according to claim 1, wherein the catalyst is dispersed in the reaction medium in the form of crystals or microspheres having a particle size of between 5 and 100 micrometers whereas the cocatalyst is used in the form of powder or microspheres having a similar size distribution.

\* \* \* \* \*